(12) United States Patent
Anderson et al.

(10) Patent No.: US 7,031,769 B2
(45) Date of Patent: Apr. 18, 2006

(54) DOSAGE CONTROL ELECTRODE FOR IONTOPHORESIS DEVICE

(75) Inventors: Carter R. Anderson, Inver Grove Heights, MN (US); Russell L. Morris, Lindstrom, MN (US)

(73) Assignee: Birch Point Medical, Inc., Oakdale, MN (US)

( * ) Notice: Subject to any disclaimer, the term of this patent is extended or adjusted under 35 U.S.C. 154(b) by 509 days.

(21) Appl. No.: 10/371,532

(22) Filed: Feb. 21, 2003

(65) Prior Publication Data

US 2004/0167460 A1    Aug. 26, 2004

(51) Int. Cl.
   *A61N 1/30* (2006.01)
   *A61N 1/00* (2006.01)
   *A61N 1/04* (2006.01)
   *A61N 1/05* (2006.01)
   *A61M 31/00* (2006.01)

(52) U.S. Cl. .................. 604/20; 604/501; 607/115; 607/120

(58) Field of Classification Search ............. 604/20, 604/501, 890.1, 891.1; 607/2, 3, 115, 116, 607/120; 314/37, 60
See application file for complete search history.

(56) References Cited

U.S. PATENT DOCUMENTS

| | | | |
|---|---|---|---|
| 4,744,787 A | 5/1988 | Phipps et al. | |
| 5,147,297 A | 9/1992 | Myers et al. | |
| 5,320,731 A * | 6/1994 | Muller et al. | 604/20 |
| 5,405,317 A | 4/1995 | Myers et al. | |
| 5,573,503 A | 11/1996 | Untereker et al. | |
| 5,685,837 A | 11/1997 | Horstmann | |
| 6,731,977 B1 * | 5/2004 | Beck | 604/20 |
| 2003/0028170 A1 | 2/2003 | Anderson et al. | |

* cited by examiner

*Primary Examiner*—Catherine S. Williams
(74) *Attorney, Agent, or Firm*—Nikolai & Mersereau, P.A.; C. G. Mersereau

(57) ABSTRACT

An electrode assembly for use in an iontophoresis device for the transcutaneous administration of an active therapeutic species includes a base layer of conductive material which is consumed (oxidizes or reduces) preferentially to water, a first upper layer of sacrificial material coated on a first portion of the base layer wherein the sacrificial material is consumed preferentially to the conductive material of the base layer. A second upper layer of non-conducting material is coated on a second portion of the base layer, the second upper layer being spaced from the first upper layer, a narrow exposed linking area of the base layer material remaining therebetween. The exposed linking area of the base layer extends across the base layer. During operation of an associated iontophoresis device, the sacrificial material will be sequentially consumed; the first upper layer will be followed by the exposed linking area of the base layer which severs the base layer thereby breaking circuit continuity in the device.

12 Claims, 4 Drawing Sheets

DOSAGE CONTROL ELECTRODE FOR IONTOPHORESIS DEVICE

BACKGROUND OF THE INVENTION

I. Field of the Invention

The present invention relates generally to iontophoresis devices for the transdermal delivery of active agents by the use of an applied electromotive force (emf). More particularly, the present invention is directed to an electrode assembly for an associated iontophoresis device which incorporates an accurate, positive circuit breaking element that stops electrical activity in the iontophoresis device after the administration of a given total quantity of active agent.

II. Related Art

It is known to construct an iontophoresis device designed to administer a given total quantity of active agent based on the consumption of a consumable electrode leading to a break in electrical conductivity in the iontophoresis circuit. As used throughout this specification, the terms "consumable", "consumed", or the like, refer to materials that are oxidized or reduced in the operation of the corresponding iontophoresis device. Such arrangements are illustrated and described, for example, in U.S. Pat. No. 5,320,731 in which an iontophoresis device is constructed having a signal generator connected to a pair of electrodes, one of which is a limiting consumable electrode, i.e., one containing a limited quantity of material preferentially electrochemically consumed (oxidized or reduced) in relation to the other materials of the iontophoresis device. The quantity of electricity necessary for complete reaction of the material designed to be electrochemically consumed is also designed to correspond to the quantity necessary to deliver the desired amount of active material to be administered by the iontophoresis device.

The consumable electrode material is applied in the form of a coating on an insulating surface or, alternatively, on a conducting support which is unreactive, i.e., does not oxidize or reduce in the environment of the device. When the consumable material has been reacted, the material becomes non-conducting and so the current path between the pair of electrodes is severed and delivery by iontophoresis stops.

While devices heretofore developed using the principle of incorporating a consumable electrode to limit agent delivery by iontophoresis have been based on sound theory, most have had certain drawbacks which have limited their useful application. Examples of such prior art consumable electrode configurations are represented in rudimentary schematic form in FIGS. 1(a)–1(c) which are side elevational or sectional views depicting the layered structure of prior art consumable electrode models of the circuit breaking type. These models are described as consumable (oxidizable) anode assemblies or partial electrophoresis systems for the delivery of a therapeutic agent but, of course, the concepts illustrated apply equally to consumption by reduction in cathode systems.

In FIG. 1(a), an anode assembly is shown generally at 10 and includes partial top layer 12 which represents the active ingredient-containing pad, a sacrificial metal-containing electrode layer 14 and a base layer 16 which selectively may be a non-electrically conducting (insulating) material or an electrically conductive material that is not consumed in the system. The theoretical concept is that when the consumable anode material located beneath the active ingredient pad 12 is fully consumed, a break will occur in the electrical circuit of the device. This is illustrated in FIG. 1(b) where the portion 18 of the consumable metal-containing layer 14 is indicated as being having been consumed thereby breaking circuit continuity at 20. This, of course, represents the ideal situation in which the portion 18 is entirely consumed prior to the breaking or failing of the circuit.

It is well known, however, that layers of material, and particularly thin layers of material, under such circumstances are generally consumed at random which allows consumption in a manner which may well isolate a portion of the layer from the rest thereby precluding total consumption of the consumable material, and thereby also causing premature failure of the electrode. This situation is illustrated in FIG. 1(c) wherein a central portion of the layer 14 is shown consumed at 22 and, although a plan view is not shown, this consumed central portion is deemed to extend all the way across the layer thereby isolating distal portion 24 of the sacrificial material prior to full consumption as at 18 in FIG. 1(b).

The situation illustrated in FIG. 1(c) can be avoided by making the base layer 16 electrically conductive but inert with respect to being oxidized or reduced. This will allow all the desired sacrificial material to be consumed as at 18 in FIG. 1(b); however, even after this takes place, the circuit remains intact as conduction is maintained along the electrically conductive base layer. This has a potentially serious drawback in that any water in the system may thereafter be oxidized or reduced producing corresponding pH changes in the system at the surface of the layer 16. Such pH changes in the system are quite undesirable because they can cause adverse reactions with the skin of a patient to which the iontophoresis device has been applied and prevention of just such changes in pH has been a long-sought goal in the operation of such devices. Additionally, if the drug is dissolved in a water solution (as is typical) there is an abundance of water present and an overdosage of drug will be delivered in accordance to the amount of water electrochemically consumed.

Of course, if the base material 16 is not only conductive, but is a material that will be oxidized or reduced in the device, then this material too will be consumed in an unpredictable fashion again infusing an uncertainty as to the amount of active material that will actually be delivered by the device.

Accordingly, there is a need to provide more accurate control of the circuit breaking characteristic associated with sacrificial or consumable electrode materials in iontophoresis devices.

SUMMARY OF THE INVENTION

By means of the present invention, there is provided an electrode assembly for use in an associated iontophoresis device for the transcutaneous administration of an active therapeutic species which incorporates an accurate and positive shutoff or circuit breaking device in the electrode or associated circuit structure. The electrode assembly of the present invention overcomes many of the problems and drawbacks associated with achieving full consumption of electroactive electrode species to be consumed and, which, at the same time, provides a separate device, the function of which is a positive and rapid severing of the circuit after consumption of the electrode species.

The present invention includes an electrode assembly for an iontophoresis device utilized in the transcutaneous administration of an active therapeutic species which involves a layered structure designed to be incorporated in a conventional iontophoresis circuit. The layered structure includes a base layer of conductive material which reacts (oxidizes or reduces) preferentially to the oxidation or reduction of water. Portions or sections of the base layer are coated with two upper layers which cover different portions of the base layer with a narrow strip of uncoated base layer remaining therebetween. The first upper layer contains the sacrificial or consumable material of the consumable electrode and is coated on the first portion or area of the base layer. The consumable material of the first upper layer is selected to be one which oxidizes or reduces in preference to the conductive material of the base layer so that during the operation of the circuit of the iontophoresis device, this material is consumed first. Part of the base layer is also covered by a second upper layer of non-conductive or insulating material coated on a second portion of the base layer, the second upper layer being spaced from the first upper layer to expose a narrow gap or linking area therebetween of exposed base layer material.

It is an important aspect of the invention that when electrical current flows through the circuit of an iontophoresis device incorporating the electrode assembly of the invention, consumption of the consumable materials will take place in a predetermined ordered sequence. The upper layer of consumable or sacrificial material will be consumed first followed by the exposed narrow linking area of the base layer between the consumable material of the upper layer and the non-conducting or insulating material coated on the second portion of the base layer. Consumption of the much smaller narrow exposed linking area of the base layer serves to sever the base layer thereby breaking electrical circuit continuity in the base layer and the corresponding iontophoresis device. By design, the portion of the base layer underneath the first upper layer is not consumed, and serves to provide sound continuous electrical contact to the first upper layer during consumption of the consumed species of that layer.

An optional non-electrically conductive substrate layer may be utilized beneath the base layer, if desired. In addition, a conductive but non-reactive layer of material may also be placed between the base layer and the first or consumable upper layer. In any event, a conductive layer exists beneath the entire area covered by the upper layer of sacrificially consumable material assuring that it will be consumed in its entirety. In addition, the materials of construction are selected so that the first upper layer of sacrificial or consumable material will also react in preference to the material of the base layer so that the first upper layer of sacrificial or consumable material will be entirely consumed prior to the consumption of any of the exposed base layer.

Preferably, the amount of consumable material in the upper layer of consumable or sacrificial material amounts to a larger quantity than that exposed in the narrow exposed linking area of the base layer. It typically is designed to be consumed when a designated dosage of active agent has been administered by the corresponding iontophoresis system. The narrow exposed linking area of the base layer is preferably very narrow and thin and, therefore, quickly consumed. In this manner, the great bulk of the consumable material is contained in the electrode coating itself while the narrow exposed linking area, which might be described as a "wear bar", serves more particularly as a circuit breaking device to turn the system off after electrode consumption.

It should further be noted that the electrode assembly of the invention can be either an anode assembly in which the consumable materials are oxidized and are used up in order of their appearance in the electromotive series or cathode electrode in which the consumable materials are reduced preferentially to each other in the same manner. They, of course, must be electrically conducting in the unreacted state and non-conducting in the reacted state in accordance with the invention. Thus, consumable electrodes of the cathode type are normally chosen from salts which are conductive in oxidized form and non-conductive in reduced form. Conversely, the consumable anode materials are normally chosen from metals which are readily consumed by electrochemical oxidation, for example, Al, Cu, Mg, Zn and Ag. The most preferred anode materials include Zn in the consumable upper layer of sacrificial material and Ag in the base layer, also forming the narrow exposed linking area of the base layer. These materials can be used alone or mixed with non-reactive constituents so long as the matrix remains conductive. Such binder materials are well known in the art.

The use of a conductive non-reactive layer between the base layer and the first upper layer of consumable or sacrificial material further ensures that the entire amount of consumable or sacrificial material will be reacted prior to the reaction of the underlying base layer and maintains the circuit breaking effect of the narrow exposed linking area. Of course, the non-reactive conductive layer like the base layer will be disconnected by the consumption of the narrow exposed linking area. Examples of these materials include platinum, titanium, stainless steel, gold, carbon, graphite and conducting polymers.

BRIEF DESCRIPTION OF THE DRAWINGS

In the drawings, wherein like numerals designate like parts throughout the same.

DETAILED DESCRIPTION

The detailed description contains examples of possible configurations of the electrode assembly of the invention and these are meant by way of example only and not intended to be limiting in any manner as variations will occur to those skilled in the art.

Figure 1A:
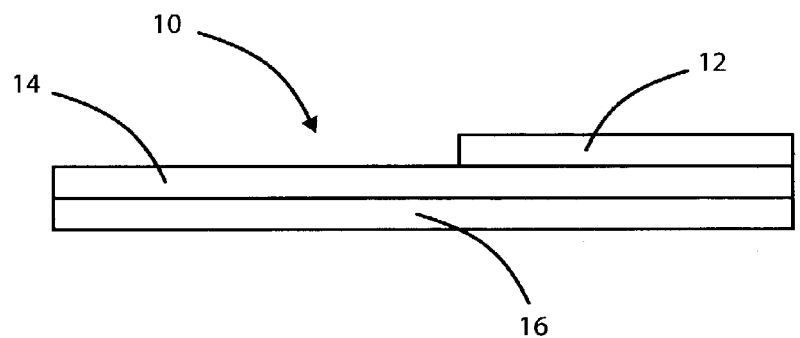
FIG. 1(a) depicts in a simplified schematic form an embodiment of a prior art anode that uses a sacrificial middle layer to limit capacity.
Figure 1B:
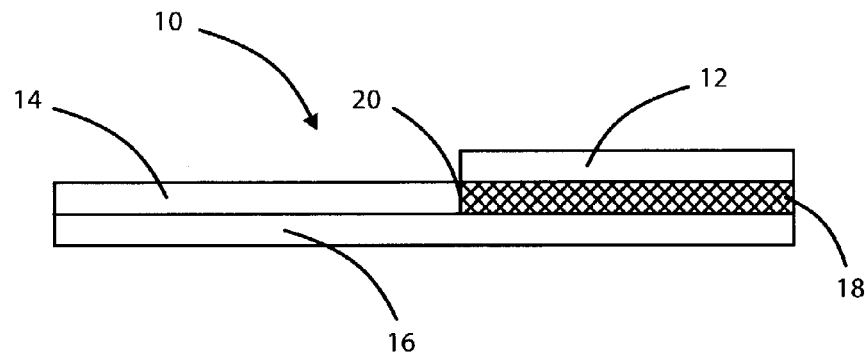
FIG. 1(b) depicts the designed ideal failure mode for the consumable anode of FIG. 1(a)
Figure 1C:
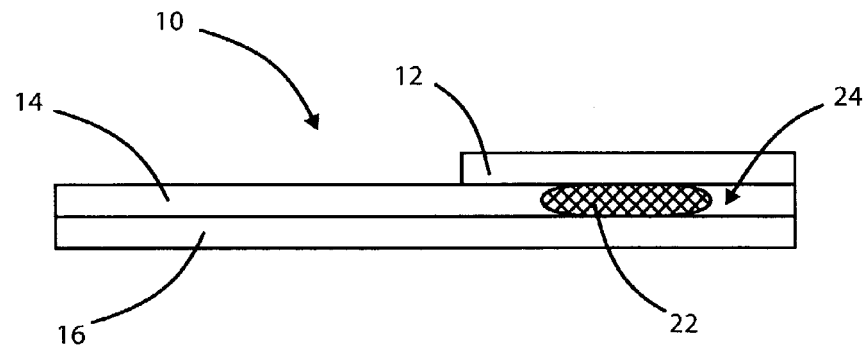
FIG. 1(c) depicts a probable failure mode for the anode of FIG. 1(a)
Figure 2A:
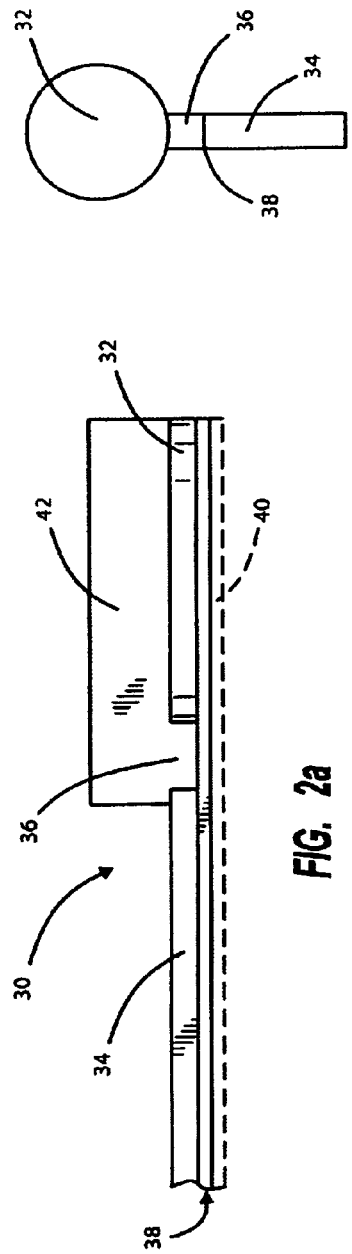
FIG. 2(a) is also a simplified schematic representation in side elevation of one embodiment of a drug delivery anode electrode portion of an iontophoresis device fabricated in accordance with the present invention.
Figure 2B:
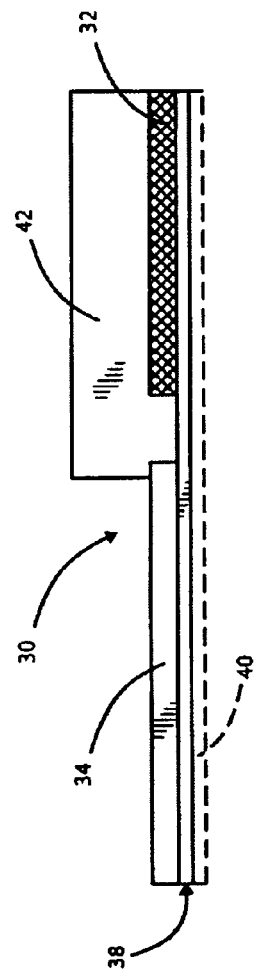
FIG. 2(b) is a greatly reduced plan view of the electrode assembly of FIG. 2(a) showing the relative sizes of the sacrificial metal layer and the exposed linking area of the base layer.
Figure 2C:
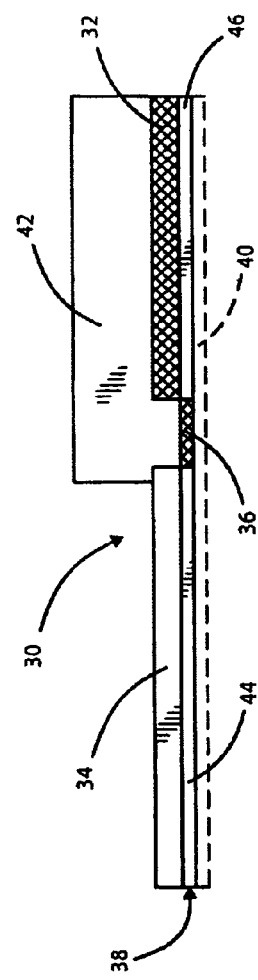
FIG. 2(c) depicts the first stage of consumption of the sacrificial metal layer of the embodiment of FIG. 2(a)
Figure 2D:
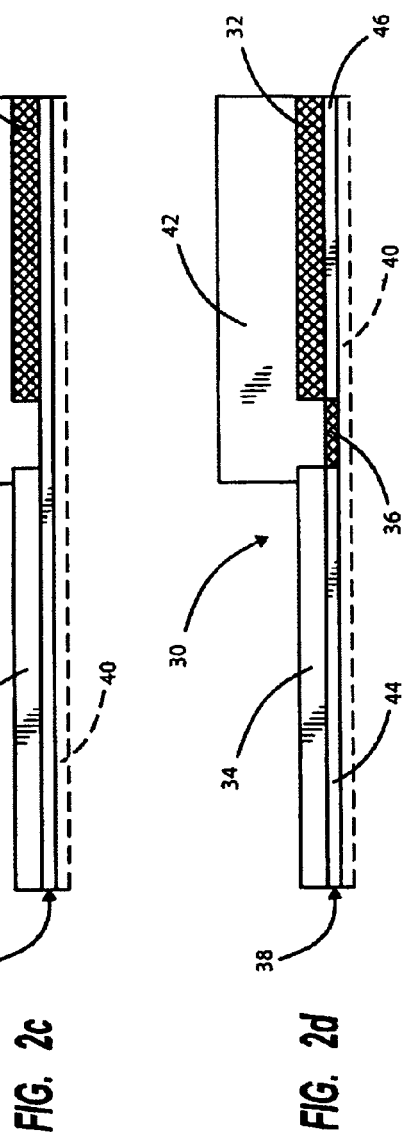
FIG. 2(d) depicts the second stage of consumption of the narrow exposed linking area severing the continuity of the circuit.

In FIGS. 2(a) and 2(b), an anode assembly is shown generally at 30 and includes a first upper layer containing consumable or sacrificial metal material at 32 which represents the initially consumed portion of the electrode assembly of the invention. The second upper layer of non-conductive material is shown at 34, there remaining a narrow gap 36 between the upper layers 32 and 34. The layers 32 and 34 are coated on a further base layer 38 and between them covering the entire area of the base layer 38 with the exception of the narrow or exposed linking area 36. A further optional non-electrically conductive substrate of a material such as Mylar (duPont) layer is depicted by the reference character 40. An overlaying portion 42 is provided which includes material for receiving an active therapeutic agent to be dispensed utilizing the iontophoresis device associated with the electrode assembly.

As seen in FIG. 2(*c*), the entire partial top layer of consumable or sacrificial metal material 32 is shown in the reacted, oxidized or consumed state. Thus, it is important to note that the entire amount of the consumable or sacrificial anode is reacted prior to the reaction of any part of the conductive base layer 38. Also, in accordance with the invention, only a small fraction of the conductive base area is consumed at all and this is only an amount sufficient to sever the continuous electrical conduction through that layer. In FIG. 2(*d*), the second stage of the dual-reacting system has been completed and the exposed narrow neck or linking area 36 of the layer 38 has been consumed and rendered non-conducting thereby severing the electrical connection between portions 44 and 46 of the base layer 38. The vast majority of layer 38 remains intact after the circuit is broken and the device ceases operation. Physical continuity only may be maintained through the non-conductive optional substrate layer 40.

Figure 3A:
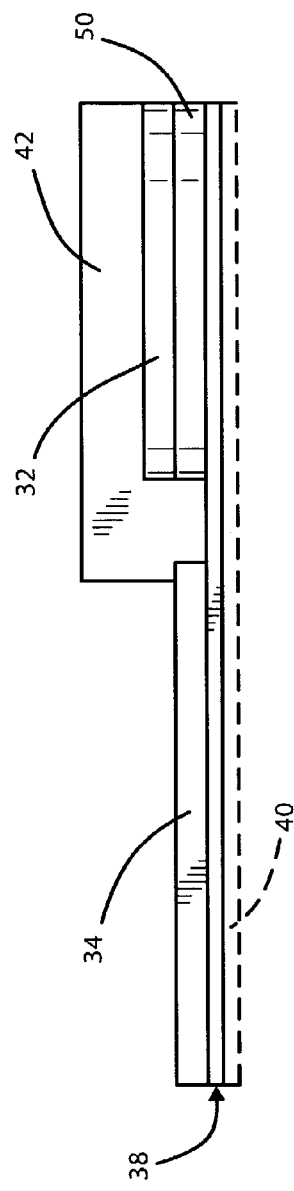
FIGS. 3(a)–3(c) are views similar to FIGS. 2(a), 2(c) and 2(d) of an alternate embodiment of the electrode assembly of the invention.
Figure 3B:
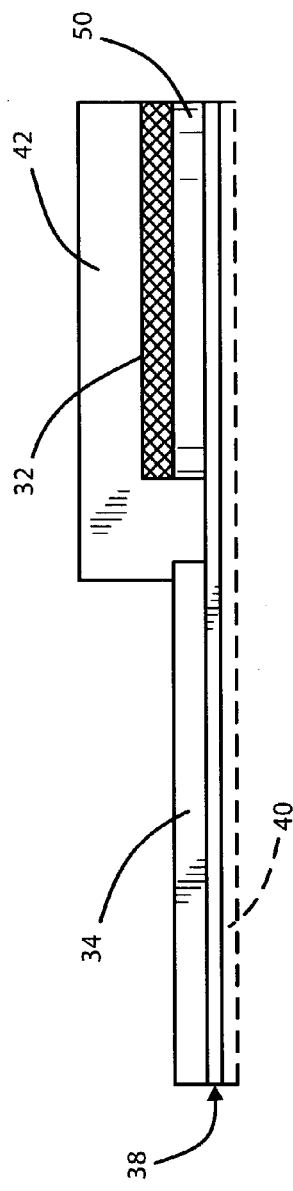
Figure 3C:
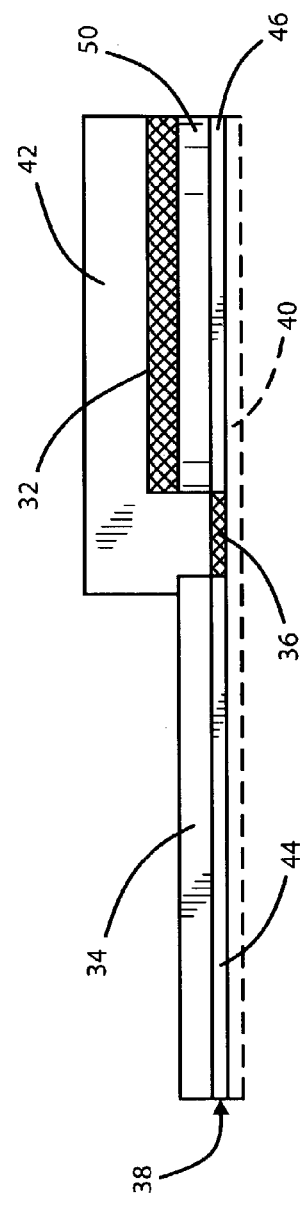

FIGS. 3(*a*)–3(*c*) depict an alternate embodiment of the electrode assembly of the invention. This embodiment is similar to the embodiments depicted in FIGS. 2(*a*)–2(*d*) with the exception that an additional conductive layer is interposed between the consumable electrode layer 32 and the base layer 38. The material of the layer 50, although conductive, is one that will not react in the iontophoresis environment and therefore remains stable and ensures total consumption of the consumable electrode material in layer 32 as the area is totally connected in the circuit. As seen in FIG. 3(*c*), the narrow exposed linking area 36 of the base layer 38 is consumed after total consumption of the electrode area 32 and this again severs the continuous circuit.

As important aspect of the present invention lies in the fact that at least two materials in descending order of reactivity are utilized to provide first, a consumable or sacrificial electrode and second, a positive circuit breaking link in the conductive base which provides a quick positive and automatically imposed shutoff system. The amount of consumable material in the consumable electrode layer 32 is large in comparison to the amount of consumable material in the linking area 36, typically in a ratio from about 20:1 to 1000:1, preferably from about 50:1 to 250:1 and most preferably it is in the order of 100:1. Thus, the transfer of active material by iontophoresis is designed to be completed during the consumption of the electrode layer 32 and the consumption of the consumable material and linking area 36 is designed solely to operate as a circuit breaker or shutoff device.

EXAMPLE I

Screen-printed Zn and AgCl were used as anode and cathode materials, respectively for an iontophoresis device. The Zn electrodes were constructed with a known amount of zinc to produce a fixed charge dosage. The configuration of the anode is illustrated in cross-section and plan views in FIGS. 2(*a*) and 2(*b*). A thick film paste, containing a known amount of Zinc and resistive binder, was printed over a silver conductive layer. In operation, as described above, after consumption of the Zn during the passage of current, an exposed portion of the base conductive layer is oxidized, severing electrical connection to the electrode.

Reproducibility and accuracy of the electrodes were tested by preparing and measuring ten iontophoretic patches, having self-limiting anodes designed to last ten milli-amp minutes. 2% sodium citrate was loaded into the anode reservoir, and 1% saline was loaded into the cathode reservoir. An integrated battery served to provide power. Current-time profiles were monitored via a voltage drop across a series resistance.

The ability of the wearable, electronic drug delivery system to administer a fixed dosage of drug was measured by delivering fentanyl into four human volunteer subjects. The study was conducted, after IRB approval, at Inveresk Clinical Research Ltd, Edinburgh Scotland. Devices designed to administer a 10 mA-min dosage over an approximately 30 minute time period were loaded with 0.5% Fentanyl Citrate in the drug reservoir, and 0.9% saline in the counter reservoir. As in the reproducibility evaluation, an integrated DC battery served as a supplemental power source, and current was monitored using an electrometer measurement of a voltage drop across a series resistor. Blood samples were collected periodically and plasma was analyzed by LC-MS/MS.

The results of the reproducibility study are summarized as follows: measured capacity of the electrodes averaged 11.3 mA-min (range 10.6 to 12.1, sd 0.49), and discharge time averaged 36.0 min (range 23 to 70, sd 13.8). The results of the Fentanyl delivery study are depicted graphically in FIGS. 4 and 5.

Figure 4:
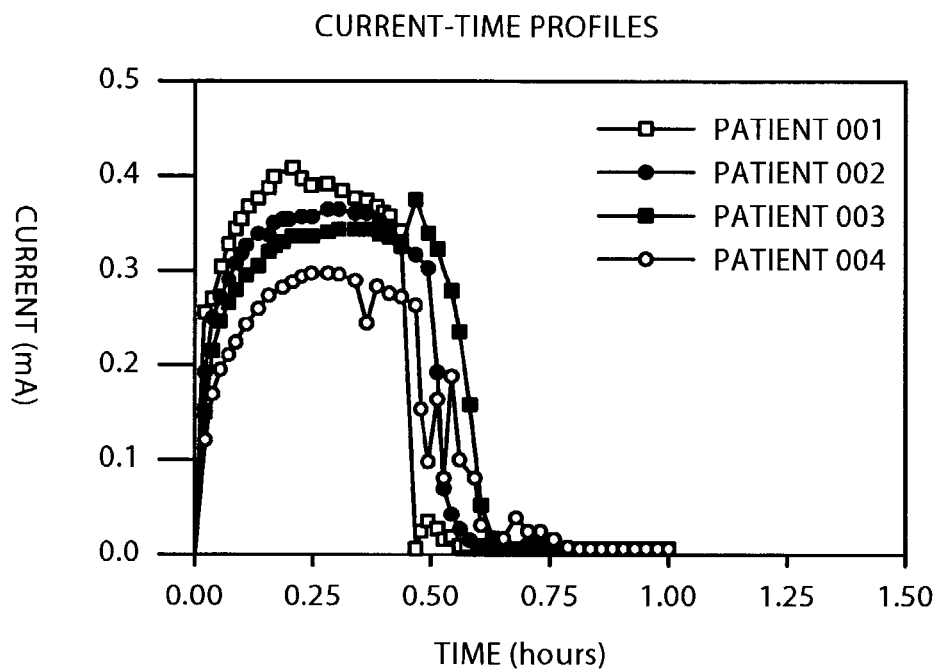
FIG. 4 represents a current-time profile for the delivery of fentanyl for patients using the system of Example I.
Figure 5:
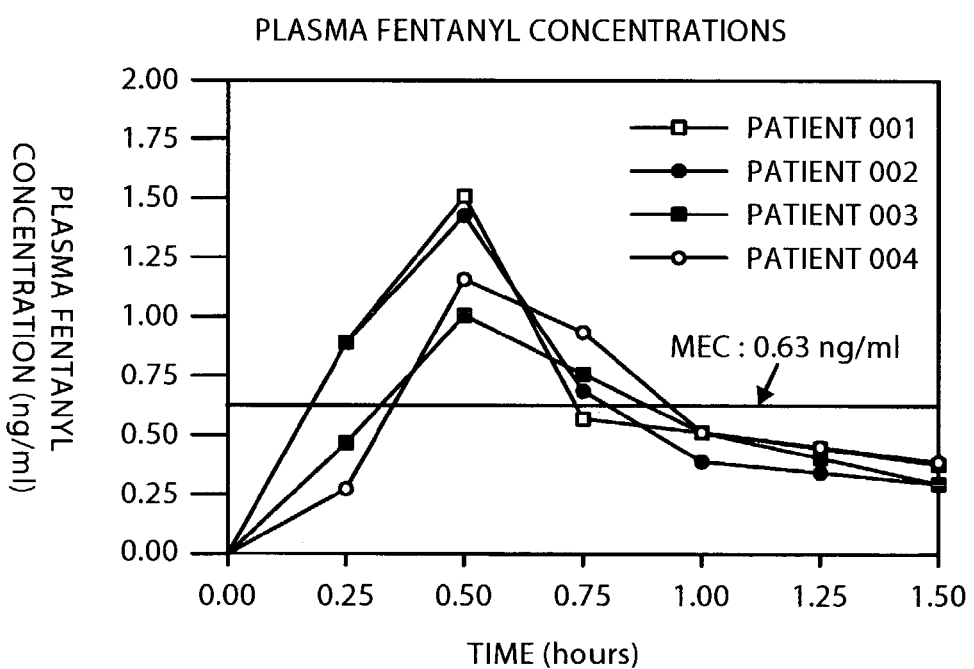
FIG. 5 depicts plasma fentanyl concentrations for the two-hour period during and immediately post-iontophoresis.

In FIG. 4, the current-time profiles for each of the four patients are displayed. In FIG. 5, plasma fentanyl concentrations are shown for the two-hour period during and immediately post-iontophoresis. The minimum effective therapeutic concentration (MEC) of fentanyl has been reported to be 0.63 ng/ml (Grond, S. et al., Clinical Pharmacokinetics of Transdermal Opioids, Clin. Pharmacokint. 2000 January 38(1); pp 59–89). This therapeutic concentration was achieved in two patients by 15 minutes, and in the remaining two by 30 minutes. In all subjects, peak fentanyl plasma concentration was achieved at 30 minutes, and was coincident with the suspension of iontophoretic current.

The devices were well tolerated in all subjects, with no adverse effects noted outside of those expected from the drug itself.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. An electrode assembly for an associated iontophoresis device in the transcutaneous administration of an active therapeutic species comprising:
   (a) a base layer of a conductive base material which oxidizes preferentially to water oxidation;

(b) a first upper layer of sacrificial electrode material coated on a first portion of said base layer wherein said sacrificial electrode material oxidizes preferentially to said conductive base material of said base layer;

(c) a second upper layer of non-conducting material coated on a second portion of said base layer, said second upper layer being spaced from said first upper layer, a narrow exposed linking area of said base layer conductive base material remaining therebetween, wherein said exposed linking area of said base layer extends across said base layer; and (d) wherein, during operation of an associated iontophoresis device, consumption of said sacrificial material is ordered with said first upper layer of sacrificial electrode material being consumed first, said exposed linking area of conducting base material of said base layer being consumed second with consumption of said linking area of conducting base material severing said base layer thereby breaking electrical circuit continuity in said base layer.

2. An electrode assembly for an iontophoresis device as in claim 1 further comprising a non-electrically conductive substrate layer beneath said base layer.

3. An electrode assembly for an iontophoresis device as in claim 1 further comprising a conductive non-oxidizing layer between said base layer and said first upper layer.

4. An electrode assembly for an iontophoresis device as in claim 2 further comprising a conductive non-oxidizing layer between said base layer and said first upper layer.

5. An electrode assembly for an iontophoresis device as in claim 1 wherein said sacrificial material of said first upper layer includes zinc and wherein said base layer of conductive material comprises silver.

6. An electrode assembly for an iontophoresis device as in claim 1 wherein said sacrificial material of said first upper layer and said conductive material of said exposed area of said base layer are in an amount corresponding to a desired amount of active therapeutic material to be transcutaneously administered by said iontophoresis device.

7. An electrode assembly as in claim 1 wherein a ratio of an amount of said sacrificial electrode material to an amount of said linking area of conducting base material is from about 20:1 to 1000:1.

8. An electrode assembly as in claim 7 wherein said ratio is about 100:1.

9. An electrode assembly for an associated iontophoresis device in the transcutaneous administration of an active therapeutic species comprising:

(a) a base layer of a conductive base material which is electrochemically consumed preferentially to water oxidation or reduction;

(b) a first upper layer of sacrificial electrode material coated on a first portion of said base layer wherein said sacrificial electrode material is electrochemically consumed preferentially to said conductive material of said base layer;

(c) a second upper layer of non-conducting material coated on a second portion of said base layer, said second upper layer being spaced from said first upper layer, a narrow exposed linking area of said base layer conductive base material remaining therebetween, wherein said exposed linking area of said base layer extends across said base layer; and (d) wherein, during operation of an associated iontophoresis device, consumption of said sacrificial material is ordered with said first upper layer of sacrificial electrode material being consumed first, said exposed linking area of conducting base material of said base layer being consumed second with consumption of said linking area of conducting base material severing said base layer thereby breaking electrical circuit continuity in said base layer.

10. An electrode assembly for an iontophoresis device as in claim 9 further comprising a non-electrically conductive substrate layer beneath said base layer.

11. An electrode assembly for an iontophoresis device as in claim 9 further comprising a conductive non-reacting layer between said base layer and said first upper layer.

12. An electrode assembly for an iontophoresis device as in claim 10 further comprising a conductive non-reacting layer between said base layer and said first upper layer.

* * * * *